US006649366B2

(12) United States Patent
Chubinskaya et al.

(10) Patent No.: US 6,649,366 B2
(45) Date of Patent: Nov. 18, 2003

(54) METHODS AND COMPOSITIONS RELATED TO MODULATORS OF ANNEXIN AND CARTILAGE HOMEOSTASIS

(75) Inventors: Susan Chubinskaya, Vernon Hills, IL (US); Jeff Hutchins, Chapel Hill, NC (US); Juergen Mollenhauer, Eisenberg (DE); Francis X. Tavares, Durham, NC (US); Stephen A. Thomson, Durham, NC (US); Jennings F. Worley, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 299 days.

(21) Appl. No.: 09/745,989

(22) Filed: Dec. 21, 2000

(65) Prior Publication Data

US 2002/0052358 A1 May 2, 2002

Related U.S. Application Data

(60) Provisional application No. 60/173,692, filed on Dec. 29, 1999.

(51) Int. Cl.[7] .................................................. C12Q 1/02

(52) U.S. Cl. .............................. 435/29; 435/4; 435/372; 424/9.321

(58) Field of Search ............................. 435/29, 4, 372; 424/9.321

(56) References Cited

U.S. PATENT DOCUMENTS 5,004,741 A 4/1991 Evans et al.
5,416,066 A 5/1995 Kaneko et al.

OTHER PUBLICATIONS

Mollenhauer, J., von der Mark, K., "Isolation and Characterization of a Collagen binding Glycoprotein from Chondrocyte Membranes," *EMBO J.*, 2(1):45–50 (1983).

Mollenhauer, J., Bee, J.A., Lizarbe, M.A., von der Mark, K., "Role of Anchorin CII, a 31,000–mol–wt Membrane Protein, in the Interaction of Chondrocytes with Type II Collagen," *J. Cell Biol.*, 98:1572–1578 (1984).

von der Mark, K., Mollenhauer, J., Mueller, P.K., Pfaeffle, M., "Anchorin CII, a Type II Collagen Binding Glycoprotein from Chondrocyte Membranes," *Ann. New York Acad. Sci.*, 469:214–223 (1985).

Fernandez, M.P., Selmin, O., Yamada, Y., Pfaeffle, M., Deutzmann, R., Mollenhauer, J., von der Mark, K., "The Structure of Anchorin CII, a Collagen Binding Protein Isolated from Chondrycte Membrane," *Biol. Chem.*, 263:5921–5925 (1988).

Böhm, B., Wilbrink, B., Kuettner, K.E., Mollenhauer, J., "Structural and Functional Comparison of Anchorin CII (Cartilage Annexin V) and Muscle Annexin V," *Arch Biochem Biophys*, 314:64–74 (1994).

Koyano Y., Hejna, M., Flechtenmacher, J., Schmid, T.M., Thonar, E.J.–M.A., Mollenhauer, J., "Collagen and Proteoglycan Production by Bovine Fetal and Adult Chondrocytes Under Low Levels of Calcium and Zinc Ions," *Connect Tiss Res*, 34(3):213–225 (1996).

King, K.B., Chubinskaya S., Reid, D.L., Madsen, L.H., Mollenhauer, J., "Absence of Cell–Surface Annexin V Is Accompanied by Defective Collagen Matrix Binding in the Swarm Rat Chondrosarcoma," *J. Cell. Biochem.* 65:131–144 (1997).

Von der Mar, K., Mollenhauer, J., "Annexin V Interactions with Collagen," *Cell. Mol. Life Sci.* 53:539–545 (1997).

Koyano, Y., HaemMerle, H., Mollenhauer, J., "Quantitative and Qualitative Analysis of 3H–Proline–Labeled Protein for the Investigation of the Collagen Metabolism by Rapid Filtration in Multiwell Plates," *BioTechniques*, 22:706–716 (1997).

Hofmann, A., et al., "Interactions of Benzodiazepine Derivatives with Annexins," *J. Biol. Chem.*, 273(5):2885–2894 (1998).

Mollenhauer, J., Mok, M.T., King, K.B.,Gupta, M., Chubinskaya, S., Koepp, H., Cole, A.A., "Expression of Anchorin CII (Cartilage Annexin V) in Human Young, Normal Adult, and Osteoarthritic Cartilage," *J. Histochem. Cytochem.*, 47(2):209–220 (1999).

Mallein–Gerin, F. et al. "Proteoglycan core protein and type II collagen gene expressions are not correlated with cell shape changes during low density chondrocyte cultures," *Differentiation* 43:204–211 (1990).

Huber, R. et al. "Crystal and Molecular Structure of Human Annexin V after Refinement" *J. Mol. Biol.* 223:683–704 (1992).

(List continued on next page.)

*Primary Examiner*—Patrick J. Nolan
(74) *Attorney, Agent, or Firm*—Michael M. Conger (57) ABSTRACT

The present invention provides a method of treating a subject with arthritis or an arthritic disease or preventing arthritis or arthritic disease in a subject, comprising administering to the subject a therapeutically effective amount of an agent that attenuates annexin function. Also provided are various methods of screening for agents and genes that increase collagen synthesis, decrease collagen degradation, or reduce or delay apoptosis, and methods of using the identified agents or nucleic acids for attaining or maintaining cartilage homeostasis, promoting cartilage repair, increasing collagen synthesis, decreasing collagen degradation, or reducing or delaying apoptosis. The invention also provides methods of decreasing mineralization of vesicles derived from chondrocytes and of promoting endochondral bone growth using agents that attenuates annexin function. The present invention also provides a composition comprising isolated chondrocytes, an agent that attenuates annexin function, and collagen fragments or other means for challenging chondrocytes, including for example, collagen fragments, collagen peptides, or immune mediators.

3 Claims, 3 Drawing Sheets

OTHER PUBLICATIONS

Raynal, P. et al. "Annexins: the problem of assessing the biological role for a gene family of multifunctional calcium– and phospholipid–binding proteins," *Biochem. Biophys. Acta* 1197:63–93 (1994).

King, K.B. et al. "Absence of Anchorin CII and Impaired collagen Binding in the Swarm Rat Chondrosarcoma," *Orthop. Res. Soc. Trans.* 20:387 (1995).

Koyano, Y. et al. "Reduced Levels of Calcium Block Hypertrophy and Degradation of Cartilage and Stimulate Collagen Synthesis in Chicken Tibial Explants," *Orthop. Res. Soc. Trans.* 21:354 (1996).

Reid, D.L. et al. "Heterogeneity of Articular Chondrocytes: Differential Binding of Collagen and Response to Collagen in Suspension Culture," *Orthop. Res. Soc. Trans.* 21:312 (1996).

Torzilli, P.A. et al. "Effects of Misoprostol and Prostaglandin E2 on Proteoglycan Biosynthesis and Loss in Unloaded and Loaded Articular cartilage Explants," *Prostaglandins* 52:157–173 (1996).

Mollenhauer, J. "Annexins: what are they good for?," *J. Cell. Molec. Life Sci.* 53:506–556 (1997).

Morgan, R.O. et al. "Annexin gene structures and molecular evolutionary genetics," *J. Cell. Molec. Life Sci.* 53:508–515 (1997).

Liemann, S. et al. "Three–dimensional structure of annexins," *J. Cell. Molec. Life Sci.* 53:516–521 (1997).

Rothhut, B. "Participation of annexins in protein phosphorylation," *J. Cell. Molec. Life Sci.* 53:522–526 (1997).

Reutelingsperger, C.P.M. et al. "Annexin V, the regulator of phosphatidylserine–catalyzed inflammation and coagulation during apoptosis," *J. Cell. Molec. Life Sci.* 53:527–532 (1997).

Donnelly, S.R. et al. "Annexins in the secretory pathway," *J. Cell. Molec. Life Sci.* 53:533–538 (1997).

von der Mark, K. et al. "Annexin V. interactions with collagen," *J. Cell. Molec. Life Sci.* 53:539–545 (1997).

Billinghurst, R.C. et al. "Enhanced Cleavage of Type II Collagen by Collagenases in Osteoarthritic Articular Cartilage," *J. Clin. Invest.* 99:1534–1545 (1997).

Mollenhauer, J. et al. *Orthop. Res. Soc. Trans.* 23:444 (1998).

METHODS AND COMPOSITIONS RELATED TO MODULATORS OF ANNEXIN AND CARTILAGE HOMEOSTASIS

This application claims priority to provisional patent application Serial No. 60/173,692, filed Dec. 29, 1999, which is incorporated herein by reference in its entirety.

This invention was made with government support under SCOR 2-P50-AR-39239 awarded by National Institute of Arthritis and Musculoskeletal and Skin Diseases of The National Institutes of Health. The government has certain rights in the invention.

BACKGROUND OF THE INVENTION

1. Field of the Invention

The present invention relates to compositions and uses of modulators of annexin and of cartilage homeostasis, including therapeutic uses in the treatment and prevention of arthritis and arthritic disease.

2. Background Art

One in seven Americans have some form of degenerative joint disease, including arthritis or arthritic disease. Arthritis and arthritic diseases include over one hundred different types of joint disease, including, for example, non-inflammatory forms, like osteoarthritis (OA), and inflammatory forms, like rheumatoid arthritis (RA). OA is the most common form of arthritis or arthritic disease, affecting over 16 million people in the United States. OA is thought to be a consequence of an attempted but failed repair of damaged cartilage tissue [3]. RA, considered to be an autoimmune disease having an unknown etiology, affects 2.1 million Americans.

In various types of arthritis and arthritic diseases, the steady-state metabolism for collagen in the extracellular matrix of articular cartilage is disturbed. This disturbance causes more degradation than synthesis of collagen, resulting in a net loss in cartilage at joint surfaces and an interruption of cartilage homeostasis. Thus, arthritis and arthritic diseases, like OA and RA, are characterized by localized proteoglycan and cartilage loss and an accompanying bone response. It has been hypothesized that destruction of collagenous extracellular matrix in subjects with arthritis is augmented by the accumulation of specific catabolic fragments of cartilage collagens that shut down matrix synthesis and activate matrix metalloproteinases [5]. There is no known cure for arthritis, and treatment is generally aimed at symptomatic relief of joint pain and stiffness using analgesics, anti-inflammatories, or injectable corticosteriods.

Annexins constitute a large family of calcium and phospholipid binding proteins. At least one example of an annexin is expressed in almost every mammalian, insect, plant, and primitive eukaryotic cell type, but no single function has been identified [1]. Calcium binding sites appear to be conserved across the various annexins.

Benzodiazepines are known to bind with high affinity to $GABA_A$ receptors in the brain and to influence chloride channel opening. The effects of various benzodiazepine derivatives include, for example, anxiolytic activities, anti-convulsant effects, cholecystokinin receptor antagonist, opiate receptor ligand, platelet-activating factor ligand, human immunodeficiency virus trans-activator Tat antagonist, and reverse transcriptase inhibitors. Recently, the in vitro interactions between various annexins and various benzodiazepine derivatives have been studied [2]. Different effects in liposomes were observed with the various benzodiazepine derivatives and the various annexins. For example, BDA452 (3-(R,S)-(L-tryptophanyl)-1,3-dihydro-1-methyl-5-phenyl-2H-1,4-benzodiazepine-2-one)inhibited calcium fluxes induced by annexins V, V-N1, VIa, and VIb but increased calcium fluxes induced by annexins I, III, and VI; whereas, BDA 250 (1,3-dihydro-1-methyl-5-phenyl-2H-1,4-benzodiazepine-2-one)) had no effect on annexin V-induced calcium influx but inhibited influx induced by annexins I and III [2]. No such benzodiazepine effect has been shown in intact cells, however, and there has been no suggestion that benzodiazepines may influence cartilage homeostasis or repair.

SUMMARY OF THE INVENTION

The present invention provides a method of treating a subject with arthritis or an arthritic disease or preventing arthritis or arthritic disease in a subject, comprising administering to the subject a therapeutically effective amount of an agent that attenuates annexin function.

Also provided are methods of screening for agents that increase collagen synthesis, decrease collagen degradation, or reduce or delay apoptosis, and methods of using the identified agents for attaining or maintaining cartilage homeostasis, promoting cartilage repair, increasing collagen synthesis, decreasing collagen degradation, or reducing or delaying apoptosis.

The invention also provides a method of decreasing mineralization of vesicles derived from chondrocytes, comprising contacting the vesicles with an agent that attenuates annexin function, and a method of promoting endochondral bone growth in a subject, comprising administering to the subject a therapeutically effective amount of an agent that attenuates annexin function.

The present invention also provides methods of screening for genes involved in modulating collagen synthesis using differential gene expression methods.

Also provided by the present invention is a method of treating a subject with arthritis or arthritic disease, comprising administering to the subject a nucleic acid that either blocks expression of the gene identified by the screening method and further identified as decreasing collagen synthesis or increasing collagen degradation, whereby cartilage homeostasis is achieved, cartilage repair is promoted, collagen synthesis is increased, or collagen degradation is decreased; or promotes expression of the gene identified by the screening method of the invention and further identified as increasing collagen synthesis or decreasing collagen degradation, whereby the nucleic acid is expressed in a cell and whereby cartilage homeostasis is achieved, collagen synthesis is increased, or collagen degradation is decreased.

The present invention also provides a composition comprising isolated chondrocytes, an agent that attenuates annexin function, and collagen fragments or other means for challenging chondrocytes, including contact with an agent that inhibits cell attachment, downregulates collagen synthesis, activates metalloproteinases, or induces cartilage breakdown, including for example, collagen fragments, collagen peptides, or immune mediators.

BRIEF DESCRIPTION OF THE DRAWINGS

Chondrocytes treated with collagen fragments alone (Col2f) had reduced levels of bound $^3$H-proline in the cell layer compared to chondrocytes cultured in the absence of collagen fragments (cells, no tr.). BDA452 reversed the effect of the collagen fragments in a dose-dependent fashion.

FIG. 2 shows the results of a calcium ion flux assay. Vesicles containing Calcium Green dye were incubated with annexin V in the presence or absence of collagen type II peptide and the presence or absence of BDA 452. Calcium Green is a calcium indicator (ex 480/em 510), whose fluorescence increases upon an increase in free calcium ions. Intravesicular fluorescence was subsequently measured to show the relative amount of calcium ion influx. After two hours, an increase in fluorescence signal was seen in the presence of annexin V and collagen peptide. BDA 452 reversed the annexin V/collagen effect on calcium ion flux.

DETAILED DESCRIPTION OF THE INVENTION

The present invention may be understood more readily by reference to the following detailed description of preferred embodiments of the invention and the Examples included therein.

Before the present methods are disclosed and described, it is to be understood that this invention is not limited to specific methods or to particular formulations, as such may, of course, vary. It is also to be understood that the terminology used herein is for the purpose of describing particular embodiments only and is not intended to be limiting.

Throughout the specification and claims, reference is made to a number of terms that are defined to have the following meanings:

"Optional" or "optionally" means that the subsequently described event or circumstances may or may not occur, and that the description includes instances where said event or circumstance occurs and instances where it does not.

The singular forms "a," "an" and "the" include single and plural referents unless the context clearly dictates otherwise.

The term "alky" is used to designate a straight or branched chain substituted or unsubstituted hydrocarbon radical containing from 1 to 12 carbon atoms.

The term "cycloalkyl" is used to represent a cyclic aliphatic hydrocarbon radical containing from 3 to 8 carbon atoms, preferably from 5 to 7 carbon atoms.

The "alkyl" groups may be substituted with one or more groups selected from hydroxy; halogen; carboxy, cyano, alkoxy, aryl, alkylthio, arylthio, aryloxy, alkoxycarbonyl, alkanoyloxy, amino, nitro, or trihalomethyl.

The term "aryl" includes carbocyclic aromatic radicals containing from 6 to 18 carbon atoms, optionally substituted with one or more substituents selected from alkyl, alkenyl, alkynyl, alkoxy, aryl, heteroaryl, halogen, alkylthio, arylthio, phosphonate, trihalomethyl, carboxy, nitro, amino, cyano, hydroxy, or acyl, where the group(s) is (are) directly attached to the aryl group. Additionally, these groups can be indirectly attached to the aryl group by a $C_{1-4}$ branched or straight chain alkyl group. Examples or aryl groups useful in the present invention include, but are not limited to, phenyl, naphthyl, and indene groups.

The term "heteroaryl" is used to represent mono- or bicyclic heteroaromatic radicals containing at least one heteroatom selected from oxygen, sulfur and nitrogen or a combination of these atoms. Examples of suitable heteroaryl groups include, but are not limited to, pyridine, furan, thiophene, pyrrole, cyclopentadiene, benzofuran, thionaphthene, indole, 2H-2-oxoindole, isoazle, pyrazine, or quinoline. Any of the heteroaryl groups can be substituted with one or more of the groups listed above with respect to aryl substitution.

The term "aralkyl" is defined as a group composed of an alkyl and an aryl group. An example of an aralkyl group is a benzyl group, which has the formula $CH_2Ph$.

The terms "alkenyl" and "alkynyl" are used to denote a substituted or unsubstituted hydrocarbon moiety having from 3 to 8 carbon atoms and containing at least one carbon-carbon double bond and one carbon-carbon triple bond, respectively.

The term halogen is used to include bromine, chlorine, fluorine and iodine. The term "trihalomethyl" is defined by the formula $CX_3$, where X is a halogen. The halogen groups of the trihalomethyl group may be the same or different.

The term "cyano" is defined as group that contains a carbon-nitrogen triple bond.

The term "acyl" refers to a group of the formula RC(O)O—, wherein R is an alkyl group, an aryl group, an aralkyl group, a cycloalkyl group, an alkenyl group, or an alkynyl group as defined above.

The term "sulfonamide group" is defined as —$SO_2NR$, wherein R is an alkyl group, an aryl group, an aralkyl group, a cycloalkyl group, an alkenyl group, or an alkynyl group as defined above.

This invention is based on the novel discovery that agents that attenuate annexin function in challenged chondrocytes can restore normal collagen synthesis. An object of the invention is to use this discovery to promote cartilage homeostasis and cartilage repair and to screen for agents and genes that promote cartilage homeostasis and cartilage repair. This invention should be of particular use in the treatment of arthritis and arthritic diseases.

The invention provides a method of treating a subject with arthritis or an arthritic disease or preventing arthritis or arthritic disease in a subject, comprising administering to the subject a therapeutically effective amount of an agent that attenuates annexin function. In one embodiment, the attenuated annexin function can be a function of an annexin that binds collagen, including, for example, type II collagen. Furthermore, the treatment can be effected by increasing collagen synthesis or decreasing collagen degradation. The increase in collagen synthesis or decrease in collagen degradation can be mediated by a growth factor. For example, in one embodiment, the agent promotes activity of an endogenous anabolic factor (e.g., OP-1) in cartilage.

As used throughout, "degenerative disease" or "arthritis or arthritic disease" refers to both inflammatory or non-inflammatory joint diseases, including, for example, osteoarthritis, rheumatoid arthritis, gout, psoriatic arthritis, reactive arthritis, viral or post-viral arthritis, spondylarthritis, juvenile arthritis, and systemic lupus erythematosus. A subject with arthritis or arthritic disease may show clinical or subclinical signs of arthritis or arthritic disease. "Osteoarthritis" or "OA," as used herein, would include both primary and secondary degenerative joint disease in both early and late stages. Thus, a subject with, including, for example, joint pain, joint swelling, joint stiffness, reduced quality and quantity of cartilage matrix, deformity, chondrocalcinosis, and reduced range of motion.

"Rheumatoid arthritis" or "RA," as used herein refers to inflammatory joint disease in both early and late stages. Signs and manifestations of the early stages can include, for example, general fatigue, joint stiffness or aching, synovial inflammation, osteoarthritis may show any of the early manifestations of osteoarthritis, including, for example, increased water content of the cartilage, increased collagen extractability, increased levels of annexin V, crepitus, and radiologic changes (including joint space narrowing, subchondral sclerosis or cysts, and osteophyte formation), or later manifestationsexcessive synovial fluid, joint effusion, osteoporosis in the ends of the bones forming the affected joint or joints, edematous synovial cells, and proliferation of synovial lining cells. In later stages, additional signs and manifestations can be detected, including joint pain, redness, swelling, and inflamation. Pannus can be seen in the joints. Cartilage and subchondral bone can be eroded at the articular surface. Changes in the composition of the synovial fluid can occur. Laxity in tendons and ligaments, as well as deformity, can occur and can cause limitations in joint range of motion and joint instability. Furthermore, Rheumatoid Factor(s) can be detected in the subject=s blood at both early and late stages of the disease.

"Treating" or "preventing" arthritis or arthritic disease means reducing or preventing one or more of the clinical manifestations. Thus, one skilled in the art would know how to determine the efficacy of treatment or prevention. A method of preventing arthritis or arthritic disease using the methods provided herein would prevent or delay early manifestations. The method of preventing OA, for example, would be indicated in middle-aged to elderly subjects, subjects who have experienced joint trauma (including arthroscopy or other surgical procedures on a joint), subjects who are overweight, subjects with joint deformity resulting in joint mal-alignment, subjects with a genetic propensity to OA (including abnormalities in collagen genes), and subjects with metabolic disorders (including alkaptonuria with ochronosis, hemochromatosis, hypothyroidism, hyperparathyroidism, and hypomagnesia), Wilson's disease, neuroarthropathy, or Paget's disease. Preventing RA, for example, may be indicated where there is a genetic predisposition to autoimmune diseases, including for example, those individuals with HLA-DR4 genetic marker.

In general, "a therapeutically effective amount of an agent" is that amount needed to achieve the desired result or results, i.e., attenuating annexin function, increasing collagen synthesis, decreasing collagen degradation, decreasing calcium influx, reducing or delaying apoptosis, promoting endochondral bone growth, attaining or maintaining cartilage homeostasis, promoting cartilage repair, suppressing inflammatory mediators (e.g., immune mediators like IL-1) and pain activators (e.g., agents that act through prostaglandin pathways, like prostaglandin E-2, cytokines, and chemokines), or reducing or preventing arthritic symptoms (e.g., improving range of motion or decreasing pain in the affected joint; decreasing radiologic signs; decreasing RA factor; decreasing erythrocyte sedimentation rate, decreasing serum protein electrophoresis; decreasing radiologic signs). The amount necessary to achieve the desired result would preferably be an amount that acts extracellularly or extravesicularly at the level of the cellular or vesicular membrane. The cell types affected by such "a therapeutically effective amount" would include chondrocytes and other cell types (e.g., fibroblasts or macrophages) which make and release collagen degradative enzymes or synthesize collagen. One of ordinary skill in the art will recognize that the potency and, therefore, a "therapeutically effective amount of an agent" can vary for the various agents used in this invention. One skilled in the art can readily assess the potency of a candidate agent that attenuates annexin function. For example, potency can be determined by measuring an increase in collagen propeptide or proteoglycan content in the cartilage, an increase in range of motion, or a reduction in pain. In addition, potency can be determined as a function of transport of calcium (fluorescently detectable or radiolabeled) via annexin in artificial liposomes or vesicles derived from chondrocytes.

The agents used in this invention are administered to a patient in need thereof by commonly employed methods for administering agents in such a way to bring the agent in contact with cartilage. The agents of the present invention can be administered orally, parenterally, transdermally, extracorporeally, topically or the like, although oral or topical administration is typically preferred. Parenteral administration of the agents of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, subcutaneous, intramuscular, intraperitoneal, intravenous, intraarticular and intratracheal routes. A more recently revised approach for parenteral administration involves use of a slow release or sustained release system such that a constant dosage is maintained. See, e.g., U.S. Pat. No. 3,610,795, which is incorporated by reference herein. The agents can also be administered using polymer based delivery systems, including, for example, microencapsulation as described in Langer [10]. The agents of the present invention can be administered using gene therapy methods of delivery. See, e.g., U.S. Pat. No. 5,399,346, which is incorporated by reference herein. Using a gene therapy method of delivery, primary cells transfected with the gene for the agent of the present invention can additionally be transfected with tissue specific promoters to target specific organs or tissue, including, for example, cartilage. An example of a tissue specific promoter for cartilage is Col2a1 [15].

The dosage of the agent varies depending on the type of arthritis or arthritic disease, degree of arthritis or arthritic disease, weight, age, sex, and method of administration. Generally, the agents can be orally or intravenously administered in an amount of about 0.01–1000 mg/day, based on an average weight of about 60 kg. Thus, an administration regimen could include long-term, daily treatment. By "long-term" is meant at least two weeks and, preferably, several weeks, months, or years of duration. The dosage could be 0.1 $\mu$g/kg/day to 20 mg/kg/day, and any amount in between, including, for example, 1 to 10 mg/kg/day, or 5 mg/kg/day.

In one embodiment, when in vitro methods are used, the amount of BDA452 used on human chondrocytes is preferably from about 0.001 to 1000 $\mu$M, and, even more preferably, from about 0.1 to 100 nM. Necessary modifications in this dosage range may be determined by one of ordinary skill in the art using only routine experimentation given the teachings herein. See *Remington's Pharmaceutical Sciences* (Martin, E. W., ed., latest edition), Mack Publishing Co., Easton, Pa. The dosage can also be adjusted by the individual physician in the event of any complication.

The agents can be administered conventionally as compositions containing the active agent as a predetermined quantity of active material calculated to produce the desired therapeutic effect in association with the required diluent, i.e., carrier or vehicle. Depending on the intended mode of administration, the agent can be in pharmaceutical compositions in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected agent in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Thus, the compositions are administered in a manner compatible with the dosage formulation and in a therapeutically effective amount. As discussed above, precise amounts of active ingredient required to be administered depend on the judgment of the practitioner and are peculiar to each individual.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions.

As used throughout, "an agent that attenuates annexin function" is an agent that reduces at least one function of any annexin, including, for example, reducing annexin ion binding or ion channel function, reducing binding of extracellular matrix molecules to the annexins, reducing intracellular signaling by the annexin, reducing phospholipid binding, reducing annexin-induced exocytosis or endocytosis, reducing mitogenic signal transduction, downregulating expression of annexins (e.g., by reducing transcription or translation of annexins so as to reduce the number of annexin molecules in the cell membrane and the overall annexin function of the cell), or reducing annexin-mediated apoptosis. For lists of various annexin functions, see references [8] and [9]. The reduction in function can be partial or complete. For example, the function can be reduced by 100%, 90%, 80%, 70%, 60%, 50%, 40%, 30%, 20%, 10%, 1%, 0.1%, or 0.01% or any amount in between as compared to the function in the absence of the agent that attenuates annexin function. Furthermore, such reduction in annexin function can be reversible, requiring repeated or continuous treatment, or irreversible, requiring one or a limited number of treatments.

Annexins include identified annexins, for example, annexin I, II, III, IV, V, VI, VII, VIII, IX, X, XI, and XII and others identified in reference [13]. Annexins also include other, as yet unidentified, members of the annexin family, including, for example, molecules having the annexin primary structure characterized by calcium binding sites, and phospholipid binding sites, and tandem homologous domains, each of which contains the endonexin loop. Thus, an agent that attenuates annexin function can attenuate, for example, annexin II or annexin V function.

In one embodiment, compounds having the structure I are useful in the present invention as an agent to attenuate annexin function:

(I)

wherein y is from 1 to 4, wherein each $R_1$ is, independently, hydrogen, a branched or straight chain alkyl group, an alkenyl group, an alkynyl group, a branched or straight chain alkoxy group, an aryl group, an aralkyl group, a cycloalkyl group, an ester group, a substituted or unsubstituted amino group, a cyano group, an amide group, a nitro group, a hydroxy group, a halo group, a thio group, or a trihalomethyl group;

$R_2$ and $R_6$ are, independently, hydrogen, hydroxy, or branched or straight chain alkyl;

$R_3$ is hydrogen, a branched or straight chain alkyl group, or a substituted or unsubstituted aryl group;

$R_4$ is hydrogen, a branched or straight chain alkyl group, an acyl group, a cycloalkyl group, oxygen, or a group having the structure II (II)

wherein W is carbon or nitrogen; Z is oxygen or $H_2$; n is 1 or 2; and $R_7$ is a branched or straight chain alkyl group, a branched or straight chain alkoxy group, an aryl group, an aralkyl group, a cycloalkyl group, or a heteroaryl group; $R_5$ is A—$R_{10}$ or $R_{10}$, wherein A is a $C_{1-4}$ branched or straight chain alkyl group, a hydroxyalkyl group, an acyl group, an amino group, an amide group, an ester group, a keto group, a substituted or unsubstituted aryl group, a substituted or unsubstituted heteroaryl group, a sulfonamide group, or a combination thereof, or $R_5$ and $R_6$ are collectively=C(H)$R_{10}$;

wherein $R_{10}$ is substituted or unsubstituted aryl, or substituted or unsubstituted heteroaryl;

V is hydrogen, an aryl group, a heteroaryl group, an alkoxy group, an alkenyloxy group, or a monopeptide;

X is oxygen, sulfur, hydrogen, an aryl group, a heteroaryl group, an alkoxy group, an alkenyloxy group, or $NR_8$, wherein $R_8$ is hydrogen, a branched or straight chain alkyl group, a substituted or unsubstituted aryl group, or a substituted or unsubstituted heteroaryl group;

Y is carbon, oxygen, sulfur, a sulfone group, a sulfoxide group, or $NR_9$, wherein $R_9$ is hydrogen, a branched or straight chain alkyl group, an alkenyl group, an alkynyl group, a cycloalkyl group, an ester group, an amino group, an amide group, a cyano group, or a trihalomethyl group;

wherein when bond a is a double bond, then $R_3$ is present and $R_2$ is not present; or when bond a is a single bond, then $R_2$ and $R_3$ are present;

wherein when bond c is a double bond, then $R_5$ is present and $R_6$ is not present; or when bond c is a single bond, then $R_5$ and $R_6$ are present;

wherein bonds a and c are not simultaneously double bonds;

wherein when bonds b, d, and e are present, then $R_3$—E—$R_4$ is a substituted or unsubstituted alkylene group, or a substituted or unsubstituted alkylene group containing at least one heteroatom;

wherein when bond f is a double bond, then bond i and V are not present; or when bond f is a single bond, then bond i is a single bond and V is present;

wherein when bond f is a single bond or a double bond, then bonds g and h are not present; or when bond f is a single bond or a double bond, and bonds g and h are present, then F is a substituted or unsubstituted alkylene group, or a substituted or unsubstituted alkylene group containing at least one heteroatom;

and a pharmaceutically acceptable salt thereof.

In one embodiment, the agent comprises a benzodiazepine compound, a benzothiazepine compound, or a combination thereof. Examples of benzodiazepine compounds useful in the present invention are disclosed in U.S. Pat. No. 5,004,741 to Evans et al., which is incorporated herein by reference in its entirety. Evans et al. also disclose the procedures for preparing a number of benzodiazepine compounds.

In one embodiment, Y is $NR_9$, wherein $R_9$ is a branched or straight chain alkyl or aryl group. In this embodiment, the nitrogen atom of $NR_9$ is incorporated into the seven-member ring of structure I. In another embodiment, Y is carbon.

In one embodiment, Y is $NR_9$, wherein $R_9$ is a branched or straight chain alkyl or aryl group; bond f is a double bond; bonds g and h are not present; and X is oxygen. In one embodiment, Y is $NR_9$, wherein $R_9$ is a branched or straight chain alkyl group; and $R_5$ is a group having the structure III:

(III)

wherein $R_{13}$–$R_{15}$ are, independently, hydrogen, a branched or straight chain alkyl group, an acyl group, a cycloalkyl group, or an aryl group; and x is from 1 to 4, wherein each $R_{16}$ is, independently, hydrogen, a branched or straight chain alkyl group, an alkenyl group, an alkynyl group, a branched or straight chain alkoxy group, an aryl group, an aralkyl group, a cycloalkyl group, an ester group, a substituted or unsubstituted amino group, a cyano group, an amide group, a nitro group, a hydroxy group, a halo group, a thio group, or a trihalomethyl group.

In a preferred embodiment, Y is $NR_9$, wherein $R_9$ is a branched or straight chain alkyl group; and $R_5$ is a group having the structure IV:

(IV)

The line attached to the amide group of structures III and IV denotes a chemical bond and not an additional carbon atom. Thus, the amide group of structures III and IV is chemically bonded to the seven-member ring of structure I. Similarly for structure II, the line attached to the C=Z group is a bond and not an additional carbon atom. Thus, the C=Z group of structure II is chemically bonded to the nitrogen atom incorporated within the seven-member ring of structure I.

In one embodiment, Y is $NR_9$, wherein $R_9$ is a branched or straight chain alkyl or aryl group bond a is a double bond and bond c is a single bond. In another embodiment, Y is $NR_9$, wherein $R_9$ is a branched or straight chain alkyl group; y is 4; and each $R_1$ is hydrogen. In yet another embodiment, Y is $NR_9$, wherein $R_9$ is a branched or straight chain alkyl or aryl group; and $R_3$ comprises a substituted or unsubstituted phenyl group. In yet another embodiment, Y is $NR_9$, wherein $R_9$ is a branched or straight chain alkyl group; and $R_4$ is a branched or straight chain alkyl group or an acyl group.

In yet another embodiment, bonds a and f are double bonds; bond c is a single bond; bonds g and h are not present; X is oxygen; Y is $NR_9$; y is 4; each $R_1$ is hydrogen, a branched or straight chain alkyl group, an alkenyl group, an alkynyl group, a branched or straight chain alkoxy group, an aryl group, an aralkyl group, a cycloalkyl group, an ester group, a substituted or unsubstituted amino group, a cyano group, an amide group, a nitro group, a hydroxy group, a halo group, a thio group, or a trihalomethyl group; $R_3$ is a substituted or unsubstituted phenyl group; $R_4$ is a branched or straight chain alkyl group or an acyl group; and $R_5$ has the structure III.

In a preferred embodiment, the agent is 3-(R,S)-(L-tryptophanyl)-1,3-dihydro-1-methyl-5-phenyl-2H-1,4-benzodiazepine-2-one (BDA452). The structure of BDA452 is shown below in structure V.

(V)

In another embodiment of the present invention, the agent is not 1,3-dihydro-1-methyl-5-phenyl-2H-1,4-benzodiazepine-2-one which is BDA250. The structure of BDA250 is shown below in structure VI.

(VI)

Examples of benzothiazepine compounds useful in the present invention are disclosed in U.S. Pat. No. 5,416,066 to Kanecko et al., which is incorporated herein by reference in its entirety. Kanecko et al. also disclose the procedures for preparing a number of benzothiazepine compounds.

In one embodiment, Y is sulfur. In another embodiment, Y is sulfur and $R_1$ is branched or straight chain alkoxy. In yet another embodiment, Y is sulfur and $R_4$ is a group having the structure II. In a preferred embodiment, Y is sulfur and $R_4$ is structure II, wherein W is nitrogen; Z is oxygen; n is 2; and $R_7$ is $CH_2Ph$.

In one embodiment, Y is sulfur; bonds g and h are not present; bond f is a single bond; and V and X are hydrogen. In another embodiment, Y is sulfur; bonds a and c are single bonds; and bonds d and e are not present. In another embodiment, bonds a, c, and f are single bonds; bonds d, e, g and h are not present; Y is sulfur; $R_1$ is branched or straight chain alkoxy; and $R_4$ has the structure II.

In a preferred embodiment, the agent is 4-(3-(1-(4-benzyl) piperidinyl)propionyl)-7-methoxy-2,3,4,5-tetrahydro-1,4-benzothiazepine, which is K201. The structure of K201 is shown below in structure VII:

In another embodiment, additional rings can be fused to the seven-member ring of structure I. For example, when bonds b, d, and e, and bonds f, g, and h are (VII)

present, then three- to seven-member rings can be fused to the seven-member ring of structure I depending upon the selection of $R_3$—E—$R_4$ and F, respectively. The fused rings can stabilize certain compounds having the structure I. For example, when bond f is a single bond, and X is sulfur, then the fused ring formed by F can increase the binding of the resultant compound.

In one embodiment, $R_3$—E—$R_4$ and F is a substituted or unsubstituted alkylene group, or a substituted or unsubstituted alkylene group containing at least one heteroatom. Examples of unsubstituted alkylene groups include, but are not limited to, methylene, ethylene, propylene, or butylene groups. Thus, when F is a methylene group (i.e., —$CH_2$—), a three-member ring is fused to the seven-member ring of structure I. A substituted alkylene group has an organic group attached to the alkylene backbone. For example, a substituted alkylene group is represented by the formula —$CH_2CH(R)$—, where R can be any organic group listed above such as an alkyl group, aryl group, an aralkyl group, or a cycloalkyl group.

The substituted or unsubstituted alkylene group can also contain at least one heteroatom. Examples of heteroatoms include, but are not limited to oxygen, nitrogen, and sulfur. The heteroatom may be at the terminal end of the alkylene group (e.g., —$CH_2CH_2O$—), within the alkylene group (e.g., —$CH_2OCH_2$—), or both the terminal end of and within the alkylene group (e.g., —$CH_2OCH_2O$—). Additionally, the heteroatom can be attached to the backbone of the alkylene group (e.g., —$CH_2CH(OH)CH_2$—).

When the compounds represented by structure I possess basic groups, it is possible to form the corresponding salt of the compound. In one embodiment, the addition of an acid to the compound will result in the formation of the salt. The acid used to form the salt should be selected from pharmaceutically acceptable acids. Examples of salts include, but are not limited to, inorganic salts such as hydrochloride or sulfate, and organic salts, such as citrate, maleate, fumarate, benzoate, succinate, acetate, tartrate, or malate.

Additionally, salts can be formed at the nitrogen atom incorporated within the seven-member ring of structure I when bonds a or c are double bonds. For example, the imine nitrogen of BDA452 (bond a is a double bond and bond c is a single bond) can react with an acid or an alkylating agent (e.g., an alkyl halide) to produce $R_4$, where $R_4$ is hydrogen or an alkyl group, respectively. Thus, when bond a or c is a double bond, $R_4$ may or may not be present. In the case when bond a or c is a double bond, and $R_4$ is present, then the nitrogen atom incorporated within the seven-member ring of structure I is cationic.

Attaching or modifying certain groups of structure I can influence the physical properties (e.g., solubility and metabolic stability) of the agent. For example, by modifying $R_1$, it is possible to increase the in vivo stability (e.g., reduce enzymatic degradation of the agent by the liver) of the agent.

$R_1$ can be modified to be an alkyl, halogroup, trihalomethyl group, cyanogroup, a substituted or unsubstituted amino group, or a cycloalkyl group. In another example, if $R_4$ is a sterically-demanding group, it is possible to increase the ability of the agent to attenuate annexin function.

As used throughout, by "subject" is meant an individual. Preferably, the subject is a mammal such as a primate, and, more preferably, a human. Thus, the "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

Also provided by the present invention is a method of screening for an agent that increases collagen synthesis or decreases collagen degradation, comprising the steps of (a) culturing cartilage or isolated chondrocytes in the presence of collagen fragments; (b) contacting the cartilage or isolated chondrocytes with the agent to be screened; and (c) detecting proteoglycan or collagen, whereby an increase in proteoglycan or collagen indicates an increase in collagen or proteoglycan synthesis or a decrease in collagen or proteoglycan degradation. Preferably the identified agent increases collagen synthesis or decreases collagen degradation and acts to maintain cartilage homeostasis (i.e., synthesis and degradation are approximately equal) or to promote cartilage repair (i.e., synthesis exceeds degradation to increase the net amount of cartilage). An agent that increases collagen synthesis or decreases collagen degradation has the net effect of promoting cartilage repair or preventing cartilage degradation.

In the present methods, the chondrocytes are mammalian chondrocytes, and, more preferably, human chondrocytes. The chondrocytes can be isolated using techniques well known in the art from either cartilage biopsies from living donors or cartilage from cadaveric donors. By "isolated chondrocytes" is meant chondrocytes relatively devoid of other cell types. Thus, "isolated chondrocytes" can be cultures of chondrocytes containing at least about 50% or more chondrocytes compared to other cell types. As used throughout, the term "chondrocytes" can include modified cells (i.e., transfected or transduced) that demonstrate at least one characteristic of a chondrocyte, including for example, the ability to synthesis collagen, express annexin, or demonstrate calcium fluxes. The "chondrocytes" can be immortalized (e.g., chondrosarcoma cells) or non-immortalized.

The culturing step of the screening method can be performed using a cell suspension, adherent cell cultures, cells in an artifucial matrix (e.g., aliginate), or explants of tissue (e.g., cartilage). During the culturing step, the chondrocytes, either isolated or present in an explant, are challenged. Collagen fragments can be used to challenge the chondrocytes in the present invention. The collagen fragments can be, for example, fragments of collagen type II. Such fragments can be generated by collagenase digestion or can be derived from the linear amino acid sequence of collagen.

As used throughout, chondrocytes or vesicles can be challenged by collagen fragments or by a variety of means, including contact with an agent that inhibits cell attachment, downregulates collagen synthesis, activates metalloproteinases, or induces cartilage breakdown, including for example, collagen fragments, collagen peptides, immune mediators. Immune mediators include IL-1, tumor necrosis factor (TNF), interferon gamma, lipopolysaccharides (LPS), plasminogen activator, phorbol 12-myristate 13-acetate (PMA), chemokines, cytokines and pain activators like prostaglandins or prostaglandin E2. The effect of such a challenge is to increase collagen degradation, decrease collagen synthesis, or interrupt cartilage homeostasis. As used throughout, "collagen fragments" can be substituted in the invention with other agents that challenge chondrocytes. The level of collagen fragments or other agent that challenges chondrocytes or vesicles must be present at levels to effect such a challenge. Collagen fragments at a level of about 0.001, 0.01, 0.10, 1.0 mg/ml and any amount in between can challenge chondrocytes. Levels of immune mediators that challenge chondrocytes include, for example, 0.001 ng/ml to 1000 ng/ml of IL-1.

By "contacting" is meant an instance of exposure of at least one substance or cell (e.g., cartilage, chondrocyte, or vesicle) to an agent. The cell or substance can be contacted with an agent, for example, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of "contact" with a cell, group of cells, or substance is determined by the time the agent, in this case an agent that attenuates annexin function, is present at physiologically effective levels or at presumed physiologically effective levels in the medium or extracellular fluid bathing the cell. Preferably, in the screening methods of the present invention, cartilage, chondrocytes or vesicles are cultured in the presence of collagen fragments, or other means of challenging, for about 1–48 hours, and more preferably for 24 hours. Also, the chondrocytes or vesicles are preferably contacted with the agent to be screened for 1–48 hours and more preferably for 24 hours, but such time would vary based on the half life of the agent and could be optimized by one skilled in the art using routine experimentation.

Preferably, the cartilage, chondrocytes, or vesicles are challenged, e.g., by collagen fragments, collagen peptides, or immune mediators, and subsequently contacted with the agent to be screened. The challenging step and the contacting step however, may overlap temporally, entirely or in part.

The contacting step can take place in vivo or in vitro. Preferably, in the screening methods of the present invention, the contacting step takes place in vitro. Alternatively, a contacting step, by administration of the agent, in methods of treatment and prevention preferably takes place in vivo.

An agent being screened by the method of the invention that increases collagen synthesis or decreases collagen degradation would counteract, partially or totally, the effect of the collagen fragment-induced challenge to the chondrocytes. Thus, in a control culture challenged by collagen fragments, levels of proteoglycan or collagen would be reduced as compared to unchallenged cultures. In cultures that are challenged by collagen fragments and treated with the agent to be screened, levels of proteoglycan or collagen would be higher than in control cultures that were challenged by collagen fragments but lacked the agent that increases collagen synthesis or collagen degradation. Thus, when the agent to be screened increases levels of proteoglycan or collagen as compared to cultures that were challenged with collagen fragments but were not contacted with the agent, then the agent is identified as one that promotes cartilage homeostasis or repair, increases collagen synthesis, or decreases collagen degradation. Such agents are useful in the treatment and prevention methods of the invention.

By "an increase in proteoglycan or collagen" is meant an increase by as little as 1%, 2%, 3%, 4%, 5%, 10%, 20%, 30%, 40%, 50%, 60%, 70%, 80%, 90%, and 100% and up to and even exceeding 200%, 300%, 400%, 500%, 600%, as well as any values in between.

Levels of proteoglycan or collagen can be detected using a variety of techniques well known in the art. E.g., [14–19]. An increase in collagen or proteoglycan levels, for example, can be detected by culturing the chondrocytes in the presence of collagen fragments, or other agent that challenges the chondrocytes, along with a label that is incorporated into newly synthesized collagen or proteoglycan and then detecting the collagen-bound or proteoglycan-bound label in the cell layer of the culture [4]. Such a label can include, for example, $^3$H-proline, $^3$H-hydroxyproline, or $^{35}$S-sulfate. The collagen-bound or proteoglycan-bound radioactive label can then be quantified (e.g., using a liquid scintillation counter) and the amount of label compared in chondrocytes contacted with the agent to be screened and chondrocytes that are not contacted with the agent. An increase in collagen-bound or proteoglycan-bound label in the chondrocyte cell layer, as opposed to the medium, in the cultures contacted with the agent to be screened would indicate that the agent increased collagen or proteoglycan synthesis. A decrease in collagen-bound or proteoglycan-bound label in the culture medium of cultures contacted with the agent to be screened would indicate the agent decreased collagen or proteoglycan release and degradation from the chondrocyte cell layer.

In the present method of screening for an agent that increases collagen synthesis or decreases collagen degradation, rather than detecting levels of proteoglycan or collagen, collagen-induced or immune mediator-induced calcium ion influx into the chondrocyte could be detected, whereby a decrease in collagen-induced or immune mediator-induced calcium ion influx indicates an agent that increases collagen synthesis or decreases collagen degradation. Calcium influx can be detected using methods well know in the art, including for example, monitoring the calcium sensitive dye FURA-2 according to the methods of Berendes et al. [12].

Also provided by the present method is a method of attaining or maintaining cartilage homeostasis, promoting cartilage repair, increasing collagen synthesis, or decreasing collagen degradation, comprising contacting cartilage with an agent identified by the screening method of the invention.

The present invention further provides a method of screening for an agent that reduces or delays chondrocyte apoptosis, comprising the steps of (a) culturing cartilage or isolated chondrocytes in the presence of collagen fragments; (b) contacting the cartilage or isolated chondrocytes with the agent to be screened; and (c) detecting chondrocyte apoptosis, whereby a decrease in collagen-induced chondrocyte apoptosis indicates an agent that reduces or delays chondrocyte apoptosis. As discussed above, it is anticipated that chondrocytes (either isolated or in explants) can be challenged by collagen fragments as well as a variety of methods.

By "apoptosis" is meant programmed cell death that has distinctive morphological and structural features that are different from those of pathological cell death or necrosis. The apoptotic process is characterized by cell shrinkage, cell membrane blebbing, reduced adhesion to substrate, reduced cell-cell contact, nuclear fragmentation and cytoplasmic budding that leads to the formation of apoptotic bodies. Accordingly, apoptotic chondrocytes can be identified histologically and the number of apoptotic chondrocytes quantified by cell counting. Alternatively, during the early events, apoptotic chondrocytes can be identified by a loss of membrane asymmetry when phosphatidylserine is exposed on the outer leaflet of the plasma membrane (e.g., preferential annexin V binding). In the late stages of apoptosis, internucleosomal cleavage of the DNA occurs to generate monomers and multimers of DNA. These monomers and multimers can be identified as a DNA laddering effect (e.g., using kits with reagents for the isolation and electrophoretic separation of DNA fragments with high resolution). Fragments of DNA from apoptotic chondrocytes can also be detected by incorporating nucleotides at the 3' ends with TdT (e.g., TdT-biotin). Additional indicators of chondrocytic apoptosis include alterations in the expression of the Bcl-2 family of proteins, caspase activity, and cleavage of poly (ADP-ribose) polymerase (e.g., Bax, Bcl-2, Bcl-XL, caspase-2, -3, -6, -8, -9 and PARP). Other markers may include a decrease of keratin sulfate, hyluronan and collagen fragments (crosslinks) in the fluids and extracellular matrix.

The present invention also provides a method of reducing or delaying chondrocyte apoptosis, comprising contacting chondrocytes or cartilage with an agent identified by the present screening method.

Further provided by the present invention is a method of screening for an agent that increases collagen synthesis or decreases collagen degradation, comprising the steps of (a) culturing annexin-containing vesicles in the presence or absence of collagen fragments; (b) contacting the annexin-containing vesicles with the agent to be screened; and (c) detecting collagen-induced calcium ion influx or efflux, whereby an decrease in collagen-induced calcium ion influx or efflux indicates an agent that increases collagen synthesis or decreases collagen degradation. By "annexin-containing vesicles" is meant vesicles having annexin in the vesicular membrane. Thus, annexin-containing vesicles can include artificial vesicles (e.g., liposomes) prepared according to the methods known in the art. See, e.g., reference [11] which is incorporated herein by reference. Alternatively, the vesicles can be chondrocyte-derived vesicles (e.g., matrix vesicles or membranes prepared according to the method of Mollenhauer et al. [1], which is incorporated herein by reference).

As used throughout, by "collagen-induced" or "collagen fragment-induced" is meant an event, e.g., increased calcium influx into or efflux from the chondrocyte or vesicle, that occurs when the chondrocyte or vesicle is challenged by collagen fragments to decrease collagen synthesis or increase collagen degradation. As discussed above, the chondrocytes or vesicles may be challenged by a variety of means.

The present invention additionally provides a method of increasing collagen synthesis or decreasing collagen degradation, comprising contacting cartilage with an agent identified by the present screening method. Examples of such agents include BDA 452, K201, and other agents that attenuate annexin function.

Also provided is a method of increasing collagen synthesis or decreasing collagen degradation, comprising contacting cartilage with an agent that attenuates annexin function. Examples of such agents include BDA 452, K201, and other agents that attenuate annexin function.

Furthermore, the invention provides a method of decreasing mineralization of vesicles derived from chondrocytes, comprising contacting the vesicles with an agent that attenuates annexin function. Examples of such agents include BDA 452, K201, and other agents that attenuate annexin function.

The present invention also provides methods of screening for genes involved in modulating collagen synthesis using differential gene expression methods. As one embodiment, the invention provides a method of screening for genes involved in increasing or decreasing collagen synthesis or increasing or decreasing collagen degradation comprising the steps of culturing chondrocytes in the presence or absence of a means for challenging the chondrocytes (including for example, collagen fragments, collagen peptides, or an immune mediator); culturing the chondrocytes in the presence or absence of an agent that attenuates annexin function; isolating RNA from the chondrocytes; and detecting RNA present at higher or lower levels from the chondrocytes cultured in the presence of the means for challenging the chondrocytes and the agent that attenuates annexin function. Higher or lower levels of RNA in the chondrocytes from challenged cultures treated with an agent that attentuates annexin function, as compared to the chondrocytes cultured in the absence of the means for challenging the chondrocytes or the agent that attenuates annexin function, indicates genes involved in modulating collagen synthesis or collagen degradation. By "modulating collagen synthesis or collagen degradation" is meant any direct or indirect role in increasing or decreasing collagen synthesis or collagen degradation. The proteins encoded by the genes identified as modulating collagen synthesis or collagen degradation could be further identified as directly or indirectly decreasing collagen synthesis, increasing collagen degradation, increasing collagen synthesis, or decreasing collagen degradation by a variety of techniques known in the art. See, e.g., [20–21] which are incorporated herein by reference.

Methods of isolating and detecting RNA are well known in the art. See e.g., [6]. Optionally, following isolation of the RNA, the RNA can be reverse transcribed to cDNA using techniques well known in the art, and cDNA, rather than RNA, can be detected, wherein the cDNA present at higher or lower levels in chondrocytes cultured in the presence of collagen fragments or other means of challenging the chondrocytes and the agent that attenuates annexin function indicates genes involved in modulating collagen synthesis or collagen degradation. Also provided is the screening method with or without collagen fragments or other means of challenging the chondrocytes, further comprising amplifying the cDNA to produce amplification products, and comparing the amplification products of the chondrocytes cultured in the presence and absence of the agent, wherein the amplification products correlate with gene expression. The comparison of cDNA or amplification products can be performed by detecting different bands of sequence or by applying the cDNA or amplification products to gene arrays, which can be purchased commercially, for example, from Clonetech. Additional methods of isolating RNA, reverse transcribing RNA, detecting RNA, cDNA, amplifying cDNA, and comparing cDNA and amplification products are techniques well known in the art. See, for example, *Basic Cloning Procedures* (Springer Lab Manual), ed. Berzins (1998) [24] and *Molecular Cloning*, eds. Sambrook, Fritsch, and Maniatis, (1989) [6], which are incorporated by reference herein.

Also provided by the present invention is a method of treating a subject with arthritis or arthritic disease, comprising administering to the subject a nucleic acid that blocks expression of the gene identified by the screening method and further identified as decreasing collagen synthesis or increasing collagen degradation, whereby cartilage homeostasis is achieved, cartilage repair is promoted, collagen synthesis is increased, or collagen degradation is decreased. By "blocks expression" is meant any partial or complete interruption of expression of a gene, including, for example, by binding an antisense oligonucleotide to the gene or to an RNA transcript of the gene that decreases collagen synthesis or increases collagen degradation so as to prevent or reduce expression of the gene.

The present invention further provides a method of treating a subject with arthritis or arthritic disease, comprising administering to the subject a nucleic acid that encodes a protein that promotes expression of the gene identified by the screening method of the invention and further identified as increasing collagen synthesis or decreasing collagen degradation, whereby the nucleic acid is expressed in a cell and whereby cartilage homeostasis is achieved, collagen synthesis is increased, or collagen degradation is decreased. The protein encoded by the nucleic acid can be, for example, a transcription factor. As an alternative embodiment, a nucleic acid that encodes a protein that blocks expression of the gene identified by the screening method of the present invention and further identified as decreasing collagen synthesis or increasing collagen degradation could be administered to the subject. The invention also provides as another embodiment, a method of treating a subject with arthritis or arthritic disease, comprising administering to the subject a nucleic acid that encodes a protein that is also encoded by the gene identified by the screening method of the present invention as increasing collagen synthesis or decrease in collagen degradation, whereby the nucleic acid is expressed in a cell and whereby collagen synthesis is increased or collagen degradation is decreased. As used in these embodiments, the cell that expresses the desired nucleic acid can be any cell type but is preferably a chondrocyte.

In the treatment methods that involve administering to a subject a nucleic acid, the nucleic acid can be administered to the subject in a gene delivery vehicle. The gene delivery vehicle can be a virus, which can be selected from the group consisting of adenovirus, retrovirus and adeno-associated virus. Alternatively the nucleic acid can be administered to the subject in a liposome.

It is understood that nucleic acids administered to a subject would be provided in a therapeutically effective amount by a nucleic acid gene delivery vehicle. Thus, the delivery vehicle would be administered to produce a therapeutically effective amount of the desired gene product in a particular subject. For example, in a subject with osteoarthritis, a therapeutically effective amount of a gene delivery vehicle is an amount that blocks expression of a gene product that decreases collagen synthesis or increases collagen degradation or promotes expression a gene product that increases collagen synthesis or decreases collagen degradation so that cartilage homeostasis or cartilage repair is achieved.

The present invention also provides a method of promoting endochondral bone growth in a subject, comprising administering to the subject a therapeutically effective amount of an agent that attenuates annexin function. The bones of a developing subject are growing and the growth plates (also referred to as the epiphyseal plates and secondary ossification centers), where endochondral bone growth occurs, are actively forming new bone. By "promoting endochondral growth" is meant either prolonging the period of active cartilage synthesis and delaying epiphyseal plate ossification (i.e., delaying formation of an epiphyseal line) so as to result in a longer period of growth or an increase in the rate of cartilage synthesis at the epiphyseal plate so that growth occurs more rapidly. Thus, the net effect of promoting endochondral bone growth is to produce a longer bone in a subject having an active epiphyseal plate. By "active epiphyseal plate" is meant an epiphyseal plate that has not ossified into an epiphyseal line. The present method could be used to promote endochondral bone growth at one or more epiphyseal plates. In the method of promoting endochondral bone growth, the agent could attenuate annexin function on chondrocytes or vesicles derived from chondrocytes.

The present invention also provides a composition comprising isolated chondrocytes, an agent that attenuates annexin function, and collagen fragments. The agent can attenuate annexin function on either chondrocytes or vesicles derived from chondrocytes. This composition can be used in the screening methods of the invention.

As an alternative embodiment, the composition can comprise, instead of collagen fragments, any agent that challenges chondrocytes (e.g., by inhibiting cell attachment, downregulating collagen synthesis, activating metalloproteinases, or inducing cartilage breakdown, including for example, IL-1.)

The present invention also provides a method of promoting activity of an endogenous anabolic factor (e.g., OP-1) in cartilage comprising the steps of contacting the cartilage with an agent that attenuates annexin function. Activity of the endogenous anabolic factor can be promoted by several different mechanisms, e.g., by increasing synthesis of the endogenous anabolic factor or by promoting cleavage of the inactive (i.e., immature) form of the endogenous anabolic factor into an active (i.e., mature form). More specifically, the agent that attenuates annexin function preferably promotes cleavage of the pro-form of OP-1 to the mature form of OP-1.

The present invention is more particularly described in the following examples which are intended as illustrative only since numerous modifications and variations therein will be apparent to those skilled in the art.

EXAMPLES

Example I

Tissue Acquisition

Cartilage samples were dissected from the medial aspect of the dome of the talus obtained from organ donors within 24 hours of death. Samples were obtained through the Regional Organ Bank of Illinois (ROBI) and from the Department of Orthopaedic Surgery, Rush-Presbyterian-St. Luke=s Medical Center, Chicago, Ill., according to the institutions=protocols and with the institutional approvals. See, e.g., Aydelotte and Kuettner, 1988 [7].

Example II

Effect of BDA 452 on Collagen Synthesis

Human chondrocytes were isolated by overnight digestion of the tissue with pronase/collagenase. The freshly isolated chondrocytes were plated at high density ($2 \times 10^6$ cells per well) into 24-well plates and cultured in DMEM/F12+10% fetal calf serum for 48 h. The medium was then exchanged with serum-free DMEM containing $^3$H-proline and/or $^{35}$S-sulfate, and collagen fragments or IL-1 as indicated. Cells were incubated for 24 h, the medium and cell layers were harvested separately and analyzed for protein-bound $^3$H-proline, $^3$H-hydroxyproline, and $^{35}$S-sulfate [4].

Figure 1:
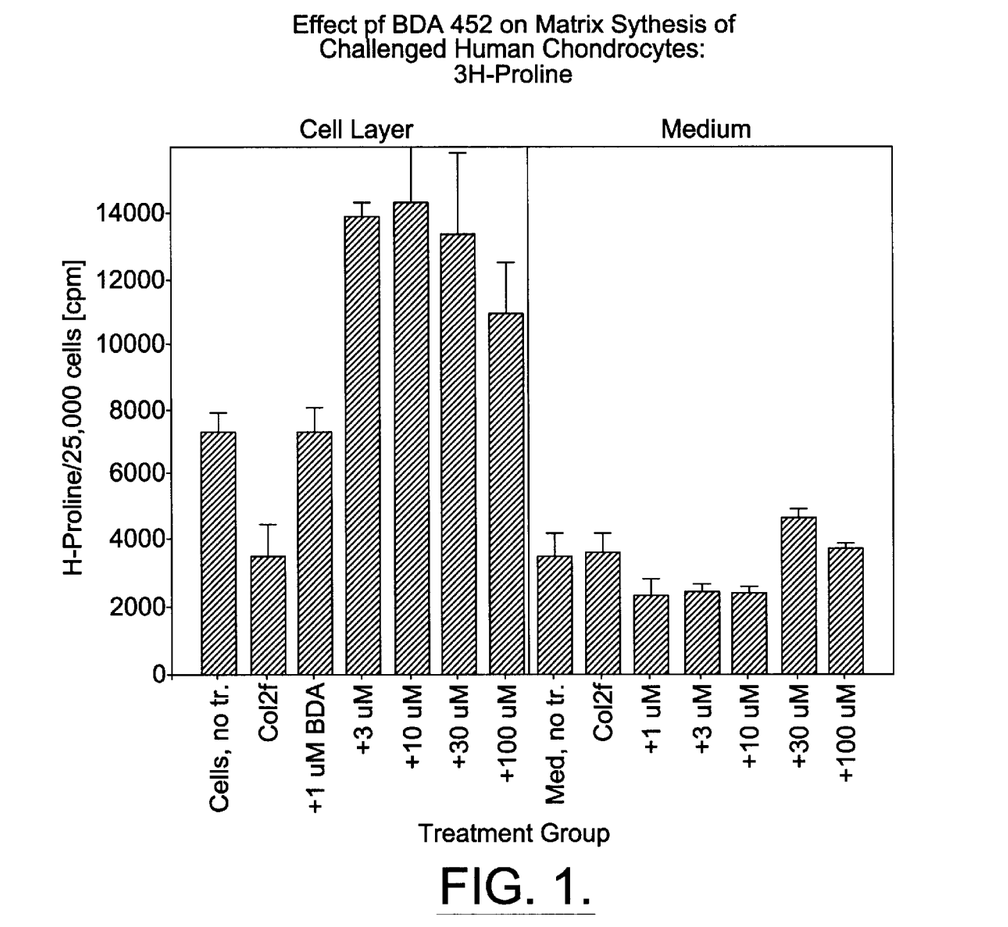
FIG. 1 shows the effect of the benzodiazepine derivative BDA452 on collagen synthesis by cultured chondrocytes challenged with fragments of collagen type II. Collagen-bound $^3H$-proline, an indicator of collagen synthesis, was measured in the cell layer (left) and the medium (right).

In cultured chondrocytes, in the presence of 0.1 mg/ml collagen peptides, protein (collagen) synthesis could be blocked by about 50% compared to untreated controls. See FIG. 1. The addition of BDA 452 reversed the effect dose-dependently. In the absence of a challenge, BDA 452 did not alter protein synthesis significantly. In extension of these findings, our data presented here suggest strongly that blockade of the annexin V gate in chondrocytes results in influencing the chondrocyte=s macromolecule metabolism. Reducing the efficiency of this channel supports the anabolic metabolism and suppresses degradative processes in the extracellular matrix. Taken together, the data suggest that controlling annexin V function, and more generally, calcium influxes, in chondrocytes may support cartilage repair mechanisms.

Example III

Calcium Ion Flux Assay

Artificial vesicles containing annexin were prepared according to methods known in the art [22]. Specifically, vesicles were prepared by drying down lipids (Avanti Polar Lipids) with nitrogen overlay. Lipids were washed once in ether and further dried under vacuum overnight. Lipids were then sonicated on ice in NMDG Buffer (150 mM N Methyl D Glucamine, and 10 mM Hepes, adjusted to ph 7.4 with HCl, then diluted to 100 mOSM with water) containing 300$\mu$M Calcium Green dye (Molecular Probes). Extravesicular dye was removed by Biobead extraction for 20 minutes.

Vesicles were diluted 1:100 in NMDG Buffer, mixed with Annexin V with or without collagen fragments (CII peptide), and incubated for 2 hours. $Ca^{++}$ fluxes were measured according to Kaneko et al. [23]. Fluorescence was measured in a 96 well plate using the Flipr plate reader.

In the presence of collagen fragments, the $Ca^{++}$ fluxes were significantly increased in artificial vesicles containing annexin V. BDA 452 inhibited these fluxes dose-dependently, both in the presence and absence of collagen fragments. These findings show that annexin V serves as a calcium gate, that the gating can be enhanced by collagen, collagen fragments, or peptides derived from the linear amino acid sequence of collagen and that the gating function can be blocked by BDA 452 [2].

Figure 2:
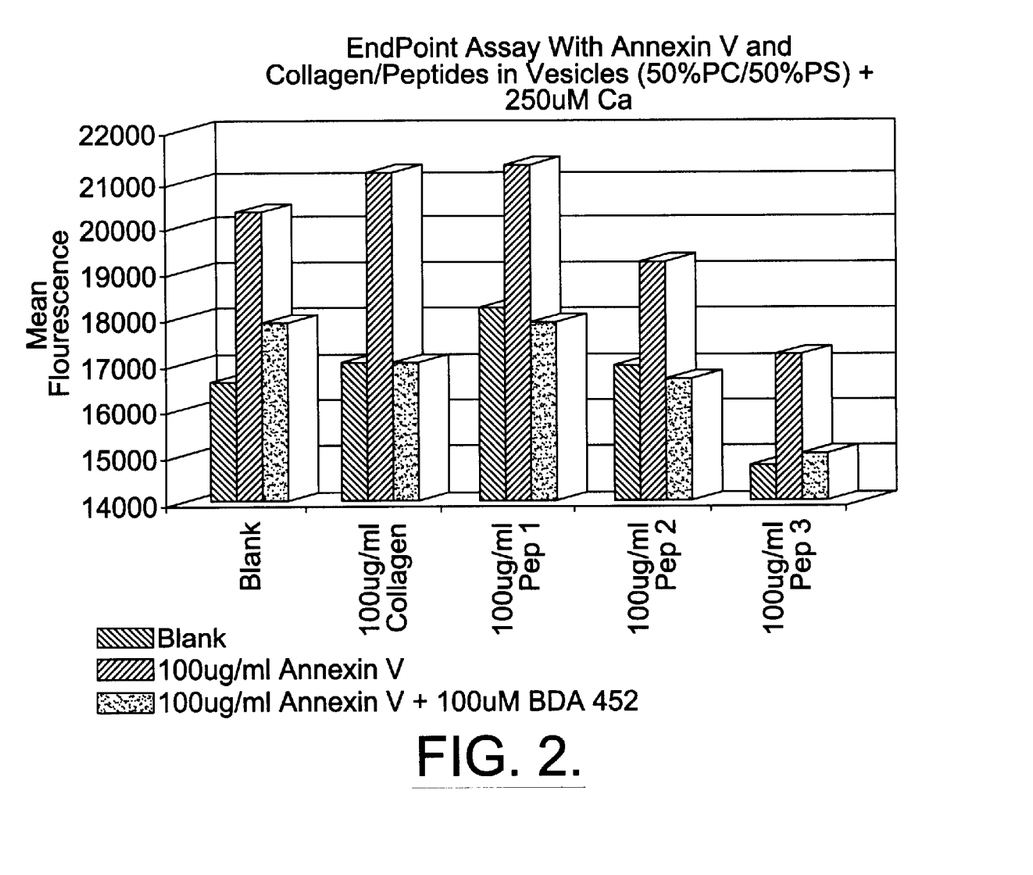

There was an initial increase in fluorescence with all samples, then a development of a CII peptide mediated signal over 2 hours. See FIG. 2 and Table I.

TABLE I

| | Fluorescence (Calcium Signal) | |
|---|---|---|
| Lipid Ratio | 180 ug/ml Annexin V | 180 ug/ml Annexin V + 100 ug/ml CII Peptide |
| 70% PS/12.5% PC/ 12.5% PE | 46454 | 57118 |
| 65% PS/12.5% PC/ 12.5% PE/5% Chol | 29023 | 42820 |

Example IV

Treatment of Arthritis

Adult patients diagnosed with osteoarthritis and having limitations in joint range of motion and/or narrowed joint spaces, as visualized radiographically, are identified. BDA452 (5 mg/kg/day) is administered orally to the patients for a three-month to two-year period. Range of motion is measured weekly to assess the efficacy of treatment. Periodic radiographic assessments are also performed.

Example V

Delaying Closure of the Epiphyseal Plate

To prolong endochondral bone growth at the epiphyseal plate of a child or adolescent, the child or adolescent is administered BDA452 (5 mg/kg/day) orally for a three-month to two-year period, corresponding to the period of prolonged growth that is desired. The status of the growth plates is assessed radiologically every month, and the height of the child or adolescent is monitored. The treatment is considered effective if the epiphyseal plate fails to close and ossify during that period of time and if the height of the child or adolescent receiving treatment continues to increase.

Example VI

Effect of BDA on Tibia Organ Cultures

The purpose of this study was to test the ability of calcium channel blocker BDA to inhibit cartilage degradation in embryonic avian tibias maintained in organ culture in the presence of lipopolysaccharide (LPS). Chick tibiotarsi were removed from 12 day embryos and their tarsal regions removed. These bones were maintained in organ culture as previously described (26–28). Four bones were placed in each well of a 24-well plate and cultured in 1 ml of DMEM supplemented with 50 μg/ml ascorbate and 10 μg/ml LPS (*E. coli* serotype 0111 :B4, catalog #L-3012, Sigma, St. Louis). The culture medium with fresh supplements was changed every other day.

BDA was dissolved in DMSO at a stock concentration of 2 mM. BDA was added to the culture medium on all feeding days and tested at two concentrations, 0.5 and 2 μM. Control cultures received an equivalent concentration of DMSO.

The loss of cartilage from the embryonic bones was measured as the release of proteoglycans and collagen (hydroxyproline) into the culture medium. The spent culture medium was collected with each medium change. The proteoglycan content of the culture medium was determined by a dimethyl methylene blue dye-binding assay (25). The hydroxyproline was measured by a colorimetric assay in 96 well plates (29).

Figure 3:
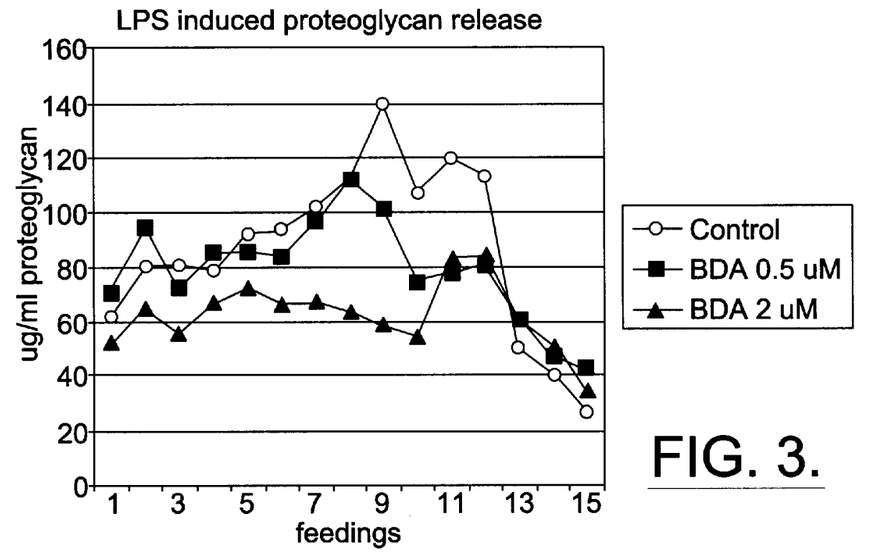
FIG. 3 shows LPS induced proteoglycan release in the presence of BDA (0.5 $\mu$M and 2.0 $\mu$M). The LPS induced release in the control cultured was greatest between feeding days 9–12 in culture. Treatment of the cultures with BDA caused a dose-dependent inhibition of proteoglycan release. The highest concentration of BDA (2 $\mu$M) showed the least release of proteoglycans to the culture medium. An intermediate amount of proteoglycan release occurred in the presence of 0.5 $\mu$M BDA compared to the DMSO carrier control.
Figure 4:
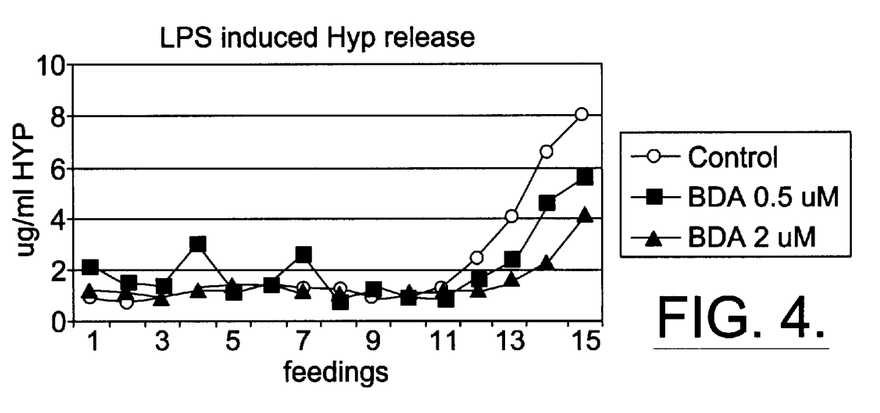
FIG. 4 shows LPS induced collagen (hydroxyproline, (Hyp)) release in the presence of BDA (0.5 $\mu$M and 2.0 $\mu$M). Treatment of the cultures with BDA caused a dose-dependent inhibition of hydroxyproline release. By feeding day 15 the DMSO control showed the greatest hydroxyproline release, while the 0.5 $\mu$M BDA had an intermediate degree of collagen release and the 2 $\mu$M BDA demonstrated the least collagen loss to the culture medium.

LPS induced cartilage loss from embryonic tibias maintained in organ culture, as evident from an increased release of hydroxyproline or proteoglycan into the culture media. Treatment of the cultures with BDA caused a dose-dependent inhibition of this cartilage loss. See FIG. 3 and 4. The proteoglycans were lost from the tissue first. The highest concentration of BDA (2 μM) showed the least release of proteoglycans to the culture medium. See FIG. 3. The 0.5 μM concentration of BDA caused an intermediate loss compared to the DMSO carrier control. A similar effect was seen on the collagen release. See FIG. 4. By feeding day 15 the DMSO control showed the greatest collagen release, while the 0.5 μM BDA had an intermediate degree of collagen release and the 2 μM BDA demonstrated the least collagen loss to the culture medium. When the collagen was lost from the cartilage tissue, the macroscopic length of the bones was diminished. The protective affect of BDA in the cultures was evident by the increased size of the bone and cartilage at the end of the experiments.

Example VII

Anabolic Effect of BDA on Normal Cartilage

Full thickness articular cartilage was dissected from load bearing regions of the femoral condyles of donors with no history of joint disease within 24 hours of death. Samples from men and women (age 50 to 76) were obtained from the Regional Organ Bank of Illinois as described above. After opening the joint, the surface of the cartilage was examined grossly. The appearance of each joint was given a grade based on the Collins scale (30) as modified by Muehleman et al (31).

Culture Conditions

Tissue explants (3×3 mm) were prepared as described above and were cultured in Dulbecco's modified Eagle's medium/Hams' F12 (1/1) containing 10 ml/L of Insulin Transferrin Selenium A (ITS, Gibco), 25 μg/ml ascorbate, and 50 μg/ml gentamicin. Experimental cultures contained either recombinant human IL-1β (Genzyme), BDA compound in DMSO, or a combination of IL-1β and BDA. ITS containing medium was used to reduce or eliminate serum-contained growth factors that could mask the released OP-1 or OP-1 degradation products and create nonspecific binding of the antibodies. To reach a steady state, cartilage explants were cultured in the absence of IL-1β or BDA for 4 days (or 96 hours) followed by two days (or 48 hours) of culture with IL-1β, BDA or both IL-1β and BDA. DMSO was added to the media control groups to account for a possible effect of DMSO.

Cartilage Extraction

Articular cartilage explants were briefly washed with 0.9% saline, homogenized and extracted in 1 M guanidine hydrochloride in the presence of proteinase inhibitors (0.1 M ε-aminocaproic acid, 0.05 M sodium acetate, 0.005 M EDTA, 0.005 M benzamidine chloride, 0.01 M N-ethylmaleimide, 0.0005 M phenymethanesulfonyl fluoride) at pH 7.4. Samples were extracted for 3 h in the refrigerator, and the extracts, together with the media, were dialyzed against water for 48 hours at 2–8° C., lyophilized and solubilized in sample buffer (0.01 M Tris HCl, pH 6.5, 1% sodium dodecyl sulfate (SDS), 10% glycerol, 0.016% bromphenol blue, 8 M urea, 0.2 M sodium chloride with (for the reduced conditions) or without (for non-reduced conditions) dithioerythritol added (DTT), pH 6.8). Cartilage extracts and media were analyzed by western blotting. All samples were normalized to the protein concentration. Protein concentrations was determined by a colorimetric assay, using BSA as a standard (Pierce, Rockford, Ill.).

Western Blot Analyses

Aliquots of samples (30 μg of protein per lane) were analyzed by electrophoresis and immunoblotting. Samples were loaded onto a 12% SDS-polyacrylamide gel (PAGE) in a buffer containing 0.2 M glycine, 25 mM Tris and 3.5 mM SDS. Proteins were transferred from SDS-PAGE gels onto nitrocellulose transfer membranes overnight at 20 V, 4–8° C. in a buffer containing 12 mM Tris (pH 7.4), 6 mM Na acetate, and 0.3 mM EDTA at pH 7.4. Immunoblot analyses was done using OP-1 antibodies. Non-specific binding sites were blocked with 5% skim milk powder (Carnation). The blots were then incubated with OP-1 primary antibodies at suggested dilutions, and a biotin-labeled goat anti-mouse IgG or anti-rabbit IgG (ImmunoPure ABC kit, Pierce, Rockford, Ill.) as a secondary antibody (1:4000 dilution). The colored reaction product was developed with alkaline phosphatase-based 1 step-NBT/BCIP substrate (ImmunoPure ABC kit, Pierce, Rockford, Ill.). To inhibit endogenous alkaline phosphatase activity, ImmunoPure Phosphatase Suppressor (Levamisole) was added to NBT/BCIP substrate in 1:100 dilution.

Western blot analysis of cartilage extracts and media confirmed the presence of endogenous OP-1 in tested samples. Importantly, the addition of BDA to the IL-1 culture led to the increase in the content of endogenous OP-1 in treated cartilage samples. Critically, this increase was primarily evident on the level of mature processed OP-1 (stronger intensity of the bands representing mature forms of OP-1, either dimer or monomer). The analysis of the culture media showed the dramatic release of pro-OP-1 on day 2 of culture in the presence of BDA that supports the data described for the cartilage. Also, BDA enhanced the release of pro-OP-1 domain, which indicates that OP-1 molecule has been processed to the mature state under these culture conditions.

In conclusion, the data indicate two major effects of BDA compound on human cartilage cultured under catabolic conditions: 1) The increase in the content of endogenous anabolic factor, cartilage OP-1, in IL-1 challenged system; 2) the processing of cartilage endogenous OP-1 from pro- into mature form.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

References

[1] Mollenhauer J, et al: J Histochem Cytochem 47:209–220 (1999)
[2] Hofmann, A, et al. J Biol Chem 273, 2885–2894 (1998)
[3] Mollenhauer, J, et al. Orthop Res Trans 23:444 (1998)
[4] Koyano Y, et al. Connect Tiss Res 34:215–225 (1996)
[5] Billinghurst, et al. J Clin Invest 99:1534–1545(1997)
[6] *Molecular Cloning*, eds. Sambrook, Fritsch, and Maniatis, (1989)
[7] Ayedelotte M B and K E Kuettner, Connect Tiss Res 18:205–222 (1988)
[8] Raynal P and Pollard H B, Biochim. Biophys. Acta 1197:63–93 (1994)
[9] Seaton B A (ed.) Annexins:molecular structure to cellular function. Book series: Molecular Biology Intelligence Unit, R.G. Landis Co., Austin, U.S.A. (1996)
[10] Langer R. "Drug delivery and targeting" Nature 392:5–10 (1998)
[11] Hofmann A et al., J. Biol. Chem. 273:2885–2894 (1998)
[12] Berendes R. et al. FEBS Lett. 317:131–134 (1993)
[13] Mollenhauer, J. Cell. Molec. Life Sci. 53:506–556 (1997)
[14] Koyano Y. et al. Connect. Tiss. Res. 34:213–225 (1996)
[15] Metsaranta M et al. J. Biol. Chem. 266:16862–16869 (1991)
[16] Mallein-Gevin F. et al. Differentiation 43:204–211 (1990)
[17] Seyer J. M. J. Lab. Clin. Med. 100:193–200 (1982)
[18] Bashey R. I. et al. Ophthalmic Res. 4:246–256 (1973)
[19] Torzilla P. A . et al. Prostaglandins 52:157–173 (1996)
[20] Fromont-Racine M. et al. Nature Genetics 16:277–282 (1997)
[21] Buckholz R. G. et al. J. Mol. Microbiol. Biotechnol. 1:135–140 (1999)
[22] Mollenhauer J. et al. J. Cell Biol. 98:1572–1579 (1984)
[23] Kaneko N. et al. Biochim. Biophys. Acta 1330:1–7 (1997)
[24] *Basic Cloning Procedures* (Springer Lab Manual), ed. Berzins (1998)
[25] Chandrasekhar, S. *Anal. Biochem.* 161:103–108 (1987)
[26] Cole, A. A., et al. *Dev. Dynamics* 193:277–285 (1992)
[27] Cole, A. A., et al. *Dev. Biol.* 159:528–534 (1993)
[28] Cole, A. A., et al. *Arthritis Rheum.* 37:1727–1734 (1994)
[29] Creemers, L. B ., et al. *BioTechniques* 22:656–658 (1997)
[30] Collins, G. H. *Pathology of Articular and Spinal Diseases*, pp. 74–115, London: Edward Arnold
[31] Muehleman, C. et al. *Osteoarthritis and Cartilage* 5:23–37 (1997)

What is claimed is:

1. A method of screening for an agent that increases collagen synthesis or decreases collagen degradation, comprising the steps of
   (a) culturing annexin-containing vesicles in the presence of collagen fragments;
   (b) contacting the annexin-containing vesicles with the agent to be screened; and
   (c) detecting collagen-induced calcium ion influx, whereby an decrease in collagen-induced calcium ion influx, as compared to collagen-induced calcium ion influx in control cultures, indicates an agent that increases collagen synthesis or decreases collagen degradation.

2. The method of claim 1, wherein the annexin-containing vesicles are liposomes.

3. The method of claim 1, wherein the annexin-containing vesicles are derived from chondrocytes.

* * * * *